(12) United States Patent
Maitre-Wilmotte et al.

(10) Patent No.: US 8,673,617 B2
(45) Date of Patent: Mar. 18, 2014

(54) **CULTURE MEDIUM FOR *HAEMOPHILUS INFLUENZAE* TYPE B**

(75) Inventors: Ghislaine Maitre-Wilmotte, Lyons (FR); Denis Speck, Lyons (FR); Bachra Rokbi, Lyons (FR)

(73) Assignee: Sanofi Pasteur SA, Lyons (FR)

( * ) Notice: Subject to any disclaimer, the term of this patent is extended or adjusted under 35 U.S.C. 154(b) by 607 days.

(21) Appl. No.: 12/170,625

(22) Filed: Jul. 10, 2008

(65) Prior Publication Data

US 2009/0017074 A1    Jan. 15, 2009

Related U.S. Application Data

(60) Provisional application No. 61/035,557, filed on Mar. 11, 2008.

(30) Foreign Application Priority Data

Jul. 10, 2007   (FR) ...................................... 07 56371

(51) Int. Cl.
C12N 1/20 (2006.01)
C12N 1/38 (2006.01)
C12P 19/00 (2006.01)

(52) U.S. Cl.
USPC ........... 435/253.6; 435/244; 435/72; 435/851

(58) Field of Classification Search
USPC ................................ 435/253.6, 244, 72, 851
See application file for complete search history.

(56) References Cited

U.S. PATENT DOCUMENTS

| 4,459,286 A | 7/1984 | Hilleman et al. |
| 5,371,197 A | 12/1994 | Marburg et al. |
| 2004/0087020 A1* | 5/2004 | Olivieri et al. ................ 435/404 |

FOREIGN PATENT DOCUMENTS

| WO | WO 97/00697 | 1/1997 |
| WO | WO 85/54296 A1 | 3/1998 |
| WO | WO 98/54296 | 12/1998 |

OTHER PUBLICATIONS

Herrington et al., "*Haemophilus influenzae* can use human transferrin as a sole source of required iron," Infection and Immunity 48(1):248-251, 1985.*
BD Bionutrients Technical Manual, 3d ed. revised, http://www.bd.com/ds/technicalCenter/index.asp, pp. 27-29, 2006.*
Needham, "*Haemophilus influenzae*: antibiotic susceptibility," Clinical Microbiology Reviews 1(2):218-227, 1988.*
Daines et al., "A Mutation in ydgQ Affects Growth and Haemolysis of *Haemophilus influenzae*," database BIOSIS & Abstracts of general meeting of the American Society for Microbiology, vol. 103 p. D-091 (2003).
Merten et al., "The New Medium MDSS2N, Free of Any Animal Protein Supports Cell Growth and Production of Various Viruses," vol. 30 pp. 191-201 (1999).
Takagi, Mickie, et al., "Improved Cultivation Conditions for Polysaccharide Production by *H. influenzae* Type B," Journal of Chemical Technology and Biotechnology, 2006, vol. 81, pp. 182-188.

(Continued)

Primary Examiner — Rosanne Kosson
(74) Attorney, Agent, or Firm — McDonnell Boehnen Hulbert & Berghoff LLP

(57) ABSTRACT

The invention relates to a culture medium for *Haemophilus influenzae* type b, characterized in that the source of protein nitrogen is of non-animal origin and comprises at least one plant peptone and in that the heme source consists of protoporphyrin IX. This medium serves in particular for the production of polyribosyl phosphate (PRP) and for the manufacture of a vaccine against *Haemophilus influenzae* type b meningitis.

23 Claims, 3 Drawing Sheets

(56) References Cited

OTHER PUBLICATIONS

Figure 1:
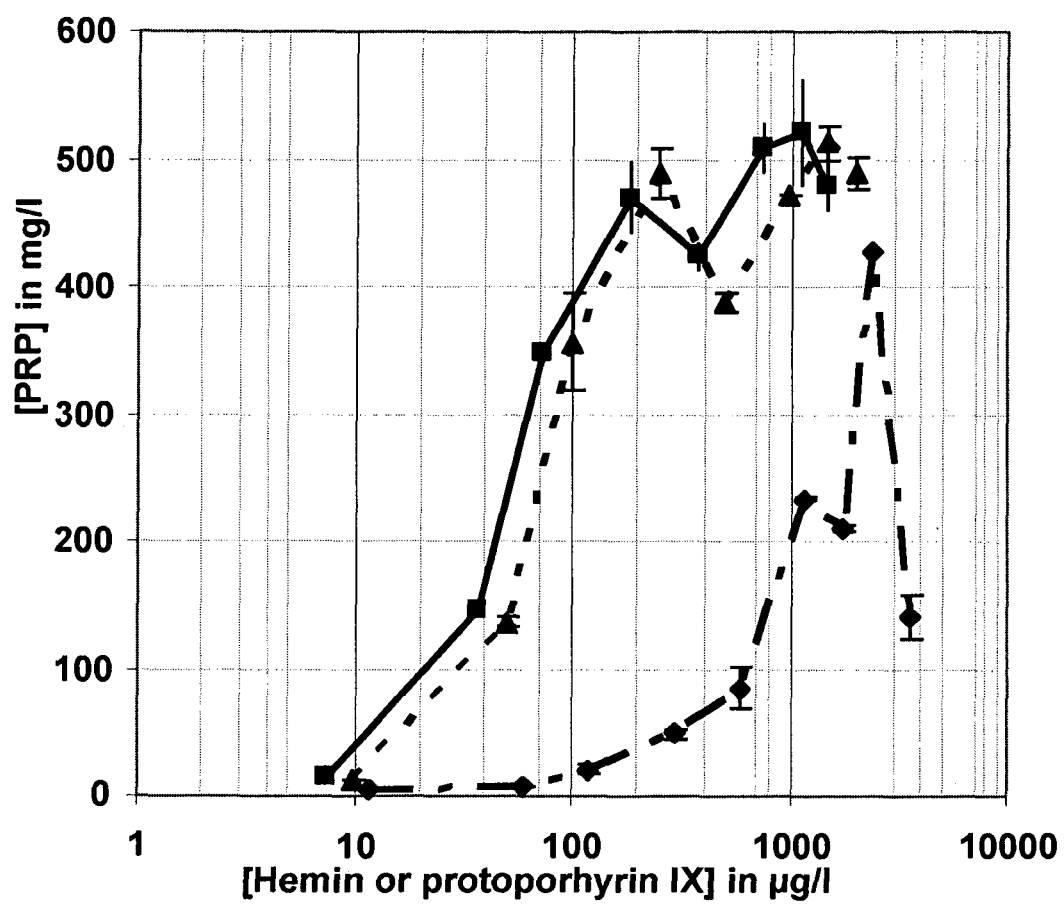

Merten, O-W, et al., "The New Medium MDSS2N, Free of Any Animal Protein Supports Cell Growth and Production of Various Viruses," Cytotechnology, 1999, vol. 30, pp. 191-201.

Susan K. Hoiseth et al.: "Genetics of Spontaneous, High-Frequencey Loss of b Capsule Expression in *Haemophilus influenzae*," Infection and Immunity, Aug. 1985, vol. 49, No. 2, pp. 389-395.

Christine E. Carty et al.: "Fermentation Studies with *Haemophilus influenzae*," Dev. Indust. Microbiology 26: 763-767 (1985).

Hasan Abdulaziz A. et al.: "Elemental iron does repress transferrin, haemopexin and heaemoglobin receptor expression in *Haemophilus influenzae*," Elsevier Science B.V.—FEMS Microbiology Letters 150; 19-26 (1997).

Joshua Merritt et al.: "Development and scale-up of a fed-batch process for the production of capsular polysaccharide from *Haemophilus influenzae*," Journal of Biotechnology 81; 189-197. (2000).

White D.C. et al.: "Hemin biosynthesis in *Haemophilus*," Journal of Bacteriology, vol. 85, pp. 842-850 (1963).

Marilyn R. Loeb: "Ferrochelatase Activity and Protoporphyrin IX Utilization in *Haemophilus influenzae*," Journal of Bacteriology, Jun. 1995, vol. 177, No. 12, pp. 3613-3615.

Mickie Takagi et al.: "Improved cultivation conditions for polysaccharide production by *H. influenzae* type b," Journal of Chemical Technology and Biotechnology 81:182-188 (2006).

\* cited by examiner

CULTURE MEDIUM FOR *HAEMOPHILUS INFLUENZAE* TYPE B

CROSS-REFERENCE TO RELATED APPLICATION

This application claims priority under 35 U.S.C. §119(e) to U.S. Application No. 61/035,557 filed Mar. 11, 2008, the disclosure of which is incorporated herein by reference in its entirety.

BACKGROUND OF THE INVENTION

1. Field of the Invention

The subject of the invention is a culture medium for *Haemophilus influenzae* type b in which the source of protein nitrogen comprises at least one plant peptone and in which the heme source consists of protoporphyrin IX. The invention also relates to a method for producing polyribosyl ribitol phosphate (PRP) used in the manufacture of a vaccine against *Haemophilus influenzae* type b meningitis.

2. Summary of the Related Art

The capsule is the major factor of virulence of *Haemophilus influenzae* type b strains. It is a polysaccharide consisting of a succession of repeating units of ribosyl ribitol phosphate. The expression polyribosyl ribitol phosphate (PRP) or capsular polysaccharide type b is used interchangeably to denote the *Haemophilus influenzae* type b capsule.

*Haemophilus influenzae* type b populations are often heterogeneous; capsulated bacteria coexist with noncapsulated bacteria. The noncapsulated bacteria have lost their capacity to express the capsule following genetic mutations which occur spontaneously. According to Hoiseth et al. (Infectious and Immunity (1985), 49: 389-395), the loss of the expression of the capsule occurs at a frequency of 0.1 to 0.3% at each bacterial generation. At the genetic level, the cap locus has been shown to be involved in the expression of the capsule at the surface of these bacteria (Kroll, J. S., et al., J. Bacteriol. (1988) 170: 859-864). The capsulated bacteria have a cap locus which contains at least two copies of an 18 Kb gene. The noncapsulated bacteria no longer have an 18 Kb gene or only a single copy of this gene. To identify the capsulated bacteria, the test of agglutination on a slide of bacteria in the presence of an anti-PRP antibody is usually used or molecular biology techniques which characterize the cap locus are used.

Vaccines based on PRP, or PRP covalently linked to a carrier protein, are used to prevent *Haemophilus influenzae* type b infections. To manufacture these vaccines, it is necessary to produce large quantities of bacteria in large volumes of culture medium from which PRP is extracted and then purified. Nevertheless, the ease with which the capsulated *Haemophilus influenzae* type b bacteria revert to noncapsulated forms can constitute a stumbling block for the production of PRP.

For the industrial production of PRP, culture media are generally used which are based on animal peptones which represent the principal source of protein nitrogen supplemented with yeast extract, glucose, hemin, β-NAD and inorganic salts. By way of example, the production medium described in U.S. Pat. No. 4,459,286 is mentioned.

Because of the risks linked to BSE, it is sought to replace products of animal origin and more particularly products of human or bovine origin with products offering better biological safety.

Carty et al. (in Dev. Indust. Microbiol. 26: 763-767 (1985)) have shown that animal peptones could be replaced by soybean peptone for the production of PRP. The composition per liter of this medium (MP medium) is the following: soybean peptone: 10 g; yeast extract: 10 ml; NaCl: 5 g; $K_2HPO_4$: 2.5 g; $Na_2HPO_4$: 3.3 g; dextrose: 5 g; hemin chloride: 10 mg; NAD: 10 mg.

Takagi et al. (J. Chem. Tech. and Biotech 81: 182-188 (2006) have sought to optimize the composition of the Carty medium (MP medium). They have shown that the PRP concentration in the culture medium could be increased by 70% to reach 0.25 g/l when the hemin and β-NAD concentrations were increased. To increase the production of PRP, it therefore appears to be necessary to increase the cofactor (hemin and β-NAD) concentrations, which are necessary for the growth of *Haemophilus influenzae* type b.

SUMMARY OF THE INVENTION

The need therefore still exists to improve the methods for producing PRP, in particular when the culture volumes are large (≥100 liters) while applying the best biological safety conditions.

Accordingly, the subject of the invention is a novel culture medium for *Haemophilus influenzae* type b, characterized in that the protein nitrogen source is of non-animal origin and comprises at least one plant peptone and in that the heme source consists of protoporphyrin IX. Such a medium is particularly suitable for the industrial production of PRP. It offers greater biological safety because peptones of animal origin have been replaced by plant peptones. It also responds to contingencies of production cost because 10 to 20 times less protoporphyrin IX than hemin is required in order to obtain PRP levels in the culture supernatants which are industrially exploitable (level≥0.2 g/l).

The inventions also provides:

- A method for producing polyribosyl ribitol phosphate (PRP) wherein all the steps are carried out by means of media free of contaminants of animal origin;
- A method for producing a population of completely capsulated *Haemophilus influenzae* serotype b bacteria;
- A method of producing PRP using a homogeneous population of capsulated *Haemophilus influenzae* serotype b bacteria obtained according to the method of the invention;
- A vaccine against *Haemophilus influenzae* type b meningitis comprising PRP obtained from one of the embodiments of the method according to the invention; and
- A solid culture medium for *Haemophilus influenzae* serotype b, the source of protein nitrogen for which is of non-animal origin.

BRIEF DESCRIPTION OF THE DRAWINGS

FIG. 1 represents the PRP production levels (in mg/l) in a of culture medium in which the peptones of animal origin have been replaced by garden pea peptone as a function of the concentrations of hemin (—◆—) or of protoporphyrin IX of animal origin (—■—) or synthetic (—▲—) origin (in μg/l).

FIG. 2 represents the PRP production levels (in mg/l) in a culture medium in which the peptones of animal origin have been replaced by wheat protein as a function of the concentrations of hemin (—◆—) or of protoporphyrin IX of animal (—■—) or synthetic (—▲—) origin (in μg/l).

FIG. 3 represents the electrophoretic profiles of various bacterial populations of *Haemophilus influenzae* serotype b: the band M represents the electrophoretic profile of a heterogeneous stock population with two bands of 18 kb and 45 kb, band F the electrophoretic profile of its daughter population (F) after selection on selective solid medium with a single band of 45 kb; the bands B represent the profiles of various white bacterial colonies (B) with a single band of 45 kb and the bands G, the various profiles of various gray bacterial colonies (G) with a single band of 18 kb.

The band MW shows the position of the molecular weight markers (kb).

DETAILED DESCRIPTION OF THE INVENTION

The expression "medium for the culture of *Haemophilus influenzae* serotype b" is understood to mean a medium favorable to the growth of *Haemophilus influenzae* serotype b and that comprises:
a source of protein nitrogen,
a heme source,
a β-NAD source
a carbohydrate source,
a source of vitamins and growth factors, and
inorganic salts.

The expression "protein nitrogen source" is understood to mean a preparation in which the quantity of amino acids, peptides, polypeptides, peptones and/or proteins represents at least 50% of the dry weight of this preparation.

The expression "protein nitrogen source of non-animal origin" is understood to mean a protein nitrogen source that has a non-animal origin. Therefore, the preparation is not produced from animal cells, animal tissues, or animal organs or bodies. It is generally produced from plants, alga, bacteria, yeasts or fungi. In a preferred embodiment, the culture media of the present invention contain no animal peptone.

The culture medium according to the invention is usually in a liquid form but it may also be in solid form. The solid form is obtained by adding a gelling substance, such as agar used generally at a concentration of 10 to 30 g/l.

The source of heme according to the invention is represented by the protoporphyrin IX of formula:

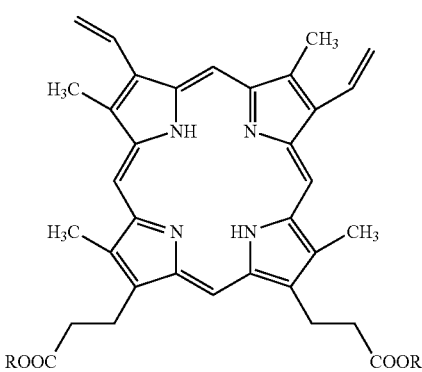

where R denotes either H or a salt, preferably an alkali metal salt, in particular a sodium salt.

Protoporphyrin IX according to the present invention is not complexed with iron. Up until now, all the media recommended for producing PRP contained, as heme source, either protoporphyrin IX complexed with iron (which is the case for heme), or a protoporphyrin IX complexed with FeCl (which is the case for hemin), or, finally and more rarely, a protoporphyrin IX complexed with FeOH (which is the case for hematin). Even if the strains of *Haemophilus influenzae* serotype b possess a ferrochelatase that allows them to convert protoporphyrin IX to a form complexed with iron (Loeb et al., J. Bacteriology (1995), 177; 3613-3615), it has never been shown that it would be possible to use as heme source non-complexed protoporphyrin IX in a culture medium based on plant peptone to produce PRP at a concentration which is industrially exploitable. Usually, it is considered that a PRP level of at least 0.1 to 0.2 g/ is required in the culture supernatant to exploit at an industrial scale the production of PRP.

Surprisingly, it has been observed that by using a protoporphyrin IX as heme source and a plant peptone as protein nitrogen source, the protoporphyrin IX concentrations necessary were 10 to 100 times lower than those which are used when the heme source is a protoporphyrin IX complexed with iron. As shown in example 1, a protoporphyrin IX concentration of between 100 and 200 µg/l is sufficient to obtain a maximum production of PRP (the concentration in the culture supernatant is 0.4 g/l) whereas a hemin concentration 10 to 20 times higher is necessary to obtain an equivalent PRP production. Moreover, at a concentration as low as 10 µg/l of protoporphyrin IX, there is still a significant production of PRP whereas it is insignificant with hemin at the same concentration. At 50 µg/l of protoporphyrin IX, the production of PRP reaches or is over than 100 µg/l (which is already a level manageable at an industrial scale) while it is about 10 µg/l or less when the medium contains hemin at the same concentration (see FIGS. 1 and 2).

Accordingly, the subject of the invention is:

A culture medium according to the invention in which the protoporphyrin IX concentration is at least 0.01 mg/l, at least 0.02 mg/l, at least 0.03 mg/l, at least 0.04 mg/l, or preferably at least 0.05 mg/l.

Preferably, the protoporphyrin IX concentration is from 0.1 mg/l to 5 mg/l, and more preferably still from 0.1 mg/l to 2 mg/l. In these preferred concentration ranges, there is advantageously an optimal production of PRP for an optimal use of the raw materials.

The protoporphyrin IX that is suitable for the subject of the invention may be of animal origin and may be produced from animal (bovine, porcine and the like) tissues. The degree of purity of these preparations is generally at least 80%, preferably at least 90%, and more preferably still at least 95% (weight/weight). Although the contaminants may contain residual quantities of amino acids, peptides and/or proteins, the preparations of protoporphyrin IX do not constitute a protein nitrogen source for the purposes of the invention because the residual quantities of amino acids, peptides and/or proteins that may be present generally represent less than 5% (and, in general, less than 1%) of the dry weight of the preparations.

Preferably, to ensure greater biological safety, a protoporphyrin IX is used which is free of contaminants of animal origin. To produce such a protoporphyrin IX, it is possible to use the method of production as described in the French patent application registered under the registration No. 07/02334 and filed on Mar. 30, 2007 and U.S. application Ser. No. 12/057,574, filed Mar. 28, 2008, and 60/943,735, filed Jun. 13, 2007 (all of which are hereby incorporated by reference) using the steps described in scheme 2 therein.

In another preferred embodiment, the culture medium according to the invention comprises a protoporphyrin IX free of contaminants of animal origin.

According to the subject of the invention, the principal source of protein nitrogen is represented by one or more plant peptones. Generally they may be in the form of hydrolysates. They may be obtained by enzymatic or chemical treatment of the proteins generally extracted from the parts of the plant that have the highest contents of proteins. Preferably, plants are used that have not been genetically modified. When chemical methods are employed, one of the methods consists in treating the protein extract with hot hydrochloric acid under pressure. The hydrolysate may be then neutralized with sodium hydroxide and then freed of solid by-products. When an enzymatic route is used, one of the classic methods consists in treating the protein extract with papain.

Plant peptones are preparations containing mainly a mixture of amino acids and of small peptides whose MW is ≤1 KD. The peptides whose MW is >1KD generally represent less than 30% of the mixture. One may also use ultrafiltered hydrolysates in order to enrich or select the small size peptides. One may also subject the ultrafiltered hydrolysate to an additional chromatography step in order to select the hydrolysate fractions according to which the majority of the peptides have a molecular weight ≤1 KD, or ≤500 Daltons or even ≤350 Daltons. In this way, one can obtain preparations of plant peptones according to which more than 40% of peptides, more than 50% of peptides, or even more than 60% of peptides have a molecular weight ≤1KD, or ≤500 Daltons or even ≤300 Daltons. The plant peptones that can be used in the context of the invention can be obtained from commercial sources, such as, for example, from potato such as those provided by Organotechnie (plant peptone E1 or plant peptone ET1), from soybean such as those provided by Organotechnie or Kerry, from cotton (Hy cotton provided by Quest), from rice (Hy rice provided by Kerry), from broad bean provided by Solabia, from wheat such as those provided by Organotechnie (wheat peptone E1) or Kerry (Hypep™ 4602, Hypep™ 4601) or from garden pea, in particular the enzyme hydrolysates of garden pea provided by Kerry (HY pea 7404) or oxoid (VG 100) or acid hydrolysates of garden pea provided by Oxoid referenced under the name "Acid hydrolyzed vegetable peptone". Preferably, the plant peptone suitable for the subject of the invention is a wheat peptone and more preferably still the plant peptone is a garden pea peptone.

To define the concentrations for using the plant peptone, account is preferably taken of the content of protein nitrogen of the peptone. This content is calculated using the Kjeldahl method (Lynch J M et al., J AOAC Int. (1999) 82(6):1389-98). Usually, the protein nitrogen contents of the plant peptones in accordance with the subject of the invention are between 8% and 15% per gram of peptone (weight/weight). In this range, good results are obtained when the plant peptone concentration in the culture medium according to the invention corresponds to a protein nitrogen concentration ranging from 0.08 to 2.25 g/l and preferably in a range of concentration ranging from 0.4 to 1.5 g/l.

Accordingly, a subject of the invention is a medium in which the total plant peptone concentration is equivalent to a protein nitrogen concentration ranging from 0.08 g/l to 2.25 g/l.

As a source of β-NAD (also called factor V or β-nicotinamide adenine dinucleotide), one can use a purified preparation of β-NAD itself or a purified preparation containing a derivative of β-NAD chosen from nicotinamide riboside (NR), β-nicotinamide adenine mononucleotide (NMN), or β-nicotinamide adenine dinucleotide phosphate (NADP). The degree of purity of the preparation is generally at least 80%, preferably at least 90% and still more preferably at least 95%. There is preferably used, in the case of the present invention, a source of β-NAD that is free of protein contaminant of animal origin. These purified preparations are used at a concentration of at least 1 μM. By way of example, β-NAD is used at a concentration ranging from 2 to 50 mg/l of culture medium.

As a source of carbohydrate, any sugar that is metabolized by *Haemophilus influenzae* type b, such as fructose, ribose, xylose, fucose, glycerol or more particularly glucose may be used. Generally, the carbohydrate source has a non-animal origin and the carbohydrate concentration in the culture medium is at least 10 mM. When glucose is used, its concentration in the culture medium is generally between 2 to 20 g/l.

The culture medium according to the invention also comprises a source of vitamins and growth factors. Toward this end, one may use a yeast extract that is obtained from the soluble fraction of the product of autolysis of brewer's yeast derived from the culture of *Saccharomyces* sp. Numerous amino acids and vitamins such as vitamins B5, B1, B2, B6, PP, H and B12, trace elements and oligo nucleotide derivatives are found in its composition. The commercially available autolytic extracts of yeast produced by Quest, Difco or Solabia are suitable for the subject of the invention.

The concentration of yeast extract in the medium according to the invention is usually within a range of concentration ranging from 0.2 g/l to 15 g/l and preferably within a range of concentration ranging from 0.2 g/l to 10 g/l and even more advantageously within a range of concentration ranging from 0.2 to 5 g/l. It has been observed that the RPR production capacity by bacteria was better when the concentration of yeast extract was in the concentration range ranging from 0.2 to 5 g/l.

The yeast extract also represents an additional source of protein nitrogen of non-animal origin. The contents of protein nitrogen in the yeast extracts are indeed generally from 9 to 11% (weight/weight). To avoid nitrogenous hypercatabolism that may be responsible for the accumulation of toxic wastes during culturing, the concentrations of plant peptone(s) and of yeast extract are generally adjusted such that the total protein nitrogen content in the medium does not exceed 2.5 g/l. Preferably, the concentrations of plant peptone(s) and of yeast extract are adjusted such that the total protein nitrogen content in the medium according to the invention is 0.5 to 2.5 g/l.

The culture medium according to the invention also comprises inorganic salts. The inorganic salts used are generally in the form of salt solutions, at least one of which exerts a sufficient buffering power for the initial pH of the medium, before inoculation of bacteria, to be preferably between 6.5 and 7.5 and more preferably between 7 and 7.5. Generally, a mixture of monovalent cations such as $Na^+$ and/or $K^+$, divalent cations such as $Ca^{++}$ and/or $Mg^{++}$, phosphate anions in $HPO_4^-$, $H_2PO_4^-$ and/or $PO_4^-$ form, and $SO_4^-$ and $Cl^-$ anions in the form of salt solutions whose molarities may vary within a concentration range ranging from $10^{-2}$ mM to 100 mM is used.

In addition to the components described in the preceding paragraphs, it is clearly understood that a culture medium according to the invention may incorporate in its composition one or more other inorganic and/or organic components provided that they do not negatively interfere with the production of PRP. Very preferably, components originating from a non-animal source are introduced. Thus, it is possible according to the invention to add to the medium amino acids produced by chemical synthesis or by microbiological fermentation, such as tryptophan and/or cysteine, inorganic nitrogen generally in the form of salt solutions providing $NH_4^+$ ions and/or even other substances such as sodium lactate. These additives are generally used at low concentrations. The amino acid supplement in the culture medium is generally at a concentration ≤1 mM. Similarly, the ammonium salts and/or the sodium lactate are generally at a concentration ≤10 mM. Finally, although it is not necessary to supplement the culture medium according to the invention by a supply of iron in the form of ionic iron because it is already present in sufficient quantity in the composition of the plant peptone and of the yeast extract, it is possible, as a precaution, to add to the culture medium a solution of iron salt, in a concentration range which may range from 0.5 to 10 mg/l in order to avoid any iron deficit which may occur during bacterial growth.

Advantageously, the culture medium according to the invention is free of any protein, polypeptide, peptide and/or amino acid of human or bovine origin or even free of any protein, polypeptide and/or amino acid of animal origin, or even more advantageously still, free of contaminants of animal origin.

According to a particular embodiment, the subject of the invention is a culture medium which comprises:
from 0.1 mg/l to 5 mg/l of protoporphyrin IX,
from 2 to 50 mg/l of β-NAD,
from 2 to 20 g/l of glucose,
from 2 to 5 g/l of a yeast extract,
a garden pea peptone equivalent to a protein nitrogen concentration of 0.4 g/l to 1.5 g/l, and
a cocktail of inorganic ions comprising $Na^+$, $NH_4^+$, $Ca^{++}$, $Mg^{++}$, $HPO_4^-$, $H_2PO_4^-$, $SO_4^-$ and $Cl^-$ ions in the form of salt solutions so that the pH of the medium is between 6.5 and 7.5, more preferably between 7.0 and 7.5.

By using this medium composition, the development of noncapsulated revertant bacteria during culturing in liquid medium is prevented. It was indeed noted that by inoculating into this medium a population that initially contains 100% of capsulated bacteria (i.e., the genome of all the bacterial population contains a cap locus which comprises two copies of the 18 kb gene), a bacterial population that still contains 100% of capsulated bacteria is obtained after a period of culture equivalent to 40 bacterial generations. This medium composition, which also encompasses the medium composition described in example 3.2.2.1 and which is used in example 4, contributes toward improving the PRP yields by exercising a stabilizing role on the population of capsulated bacteria (cf example 4).

According to another aspect, the subject of the invention is a method for producing polyribosyl ribitol phosphate (PRP) in which:
(i) *Haemophilus influenzae* serotype b is cultured in a liquid culture medium according to the invention,
(ii) the culture supernatant obtained in (i) is collected, and
(iii) the PRP is extracted from the culture supernatant.

To produce the PRP according to the method of the invention, it is possible to carry out in step (i) one or more successive *Haemophilus influenzae* serotype b cultures in a liquid medium according to the invention. The successive cultures make it possible to increase the biomass.

To do this, the bacteria obtained from a freeze-dried product or from a frozen product are inoculated into a volume of medium generally not exceeding 1 liter. After one night of culture or when the optical density of the medium is sufficient, this first culture is transferred into a second culture medium that is identical to the first, but whose volume may be up to 10 to 20 times larger. The quantity of bacteria inoculated into the second medium is adjusted such that the initial optical density (OD) of the second culture medium at 600 nm is between 0.2 and 0.4 in order to promote rapid growth of the bacterial population. This second culture is usually carried out in a fermentor but other types of containers may be used (flasks, spinners, and the like). When the culture is carried out in a fermentor, during the duration of the culture a temperature of 37° C.±1° C., constant stirring, a pressure of 0.1 bar, a pO2 of 30% and an air flow rate of 0.25 volume of gas per volume of medium per minute are usually used. It is within the ability of persons skilled in the art to choose other parameters for this type of culture. At the end of the exponential bacterial growth phase, it is possible to further amplify the biomass by transferring it into another fermentor of larger capacity using the same procedure and so on. The culture volumes obtained may be up to, or even exceed, 1000 liters. The culture(s) is(are) generally carried out according to the batch mode. It is also possible to adopt other modes of culture, in particular the fed-batch mode. In this case, a nutritive carbohydrate supplement is added to the medium during the exponential growth phase so as to prolong bacterial multiplication and to obtain, at the end of the exponential growth phase, a higher bacterial density. The quantity of carbohydrate added is evaluated as a function of the level of lactate present in the medium at the time of addition.

The supernatant of the last culture is finally collected after inactivation of the bacteria. The inactivation is conventionally carried out with the aid of a formalin solution at a final concentration of 0.35%-0.37% (v/v). The supernatant is conventionally separated from the bacteria by a centrifugation step. The PRP contained in the resulting supernatant is then extracted and purified according to conventional methods well known to persons skilled in the art.

According to another embodiment, the subject of the invention is a method for producing PRP in which:
(i) *Haemophilus influenzae* serotype b is cultured on a solid medium,
(ii) one or more colonies obtained in (i) are transferred into and cultured in a liquid culture medium according to the invention,
(iii) the culture supernatant obtained in (ii) is collected, and
(iv) the PRP is extracted from the culture supernatant.

The solid culture medium which can be used in the method of the invention should be suitable for the culture of *Haemophilus influenzae* serotype b. It comprises:
a source of protein nitrogen,
a heme source,
a β-NAD source,
a carbohydrate source,
a source of vitamins and growth factors,
inorganic salts and,
a gelling substance, usually agar at a concentration of 10 g/l to 30 g/l.

In the method for industrial production of PRP, a preliminary step of culture in solid medium is conventionally used. Usually, the bacteria obtained from a freeze-dried product or from a frozen product are resuspended and then inoculated onto a charcoal-based solid medium supplemented with horse blood. After 16 to 20 hours of culture in an incubator at 37° C. under 10% $CO_2$, bacterial colonies are collected and amplified in a liquid medium. This method has the disadvantage of using a solid medium that contains proteins of animal origin as protein nitrogen source. The inventors have therefore tried to identify compositions of solid media in which the protein nitrogen source is free of any protein of animal origin.

Initially, the inventors have demonstrated that it is possible to use a solid medium in which the yeast extract was at the same time able to serve as a protein nitrogen source, a source of vitamins and growth factors, the sources of heme, β-NAD, carbohydrate, and inorganic salts having the same features as those described above. A minimum concentration of 0.05 mg/l of protoporphyrin IX, 0.1 µM for the β-NAD source and 0.1 mM for the carbohydrate source are recommended whilst the concentration of yeast extract in the medium corresponds to a content of protein nitrogen of 0.2 to 1.5 g/l. The colonies obtained are viable even if the growth characterized by the size of the colonies is not always optimal. They may be directly transferred into a liquid culture medium according to the invention. The procedure is then carried out as above in order to amplify the culture volumes and extract and purify the PRP.

Preferably, the solid culture medium comprises as a source of protein nitrogen at least one peptone of plant origin used in the form of a chemical or enzymatic hydrolysate. In particular, it is possible to use as yeast extract supplement at least one plant peptone obtained from wheat, cotton, rice, soybean, field bean, potato, garden pea or a mixture of these at a protein nitrogen concentration range of, for example, from 0.2 g/l to 2 g/l, the total protein nitrogen concentration in the solid medium preferably not exceeding 2.5 g/l. By way of example of mixtures of plant peptones that may be used, there may be mentioned a mixture based on soybean, cotton and rice peptones, a mixture based on garden pea, cotton and wheat peptones, or a mixture based on garden pea and potato. The inventors have indeed noted that when the culture medium also comprises a plant peptone as source of protein nitrogen, bacterial growth and the viability of the bacteria were better than those observed on a charcoal-based solid medium (charcoal agar) supplemented with boiled or defibrinated horse blood. They are at a maximum when the plant peptone used is a garden pea peptone.

Accordingly, the subject of the invention is also a method for producing PRP in which the protein nitrogen source of the solid medium is free of protein of animal origin and comprises at least a plant peptone. Preferably the plant peptone is a garden pea peptone.

Advantageously, the solid culture medium according to the invention is free of any protein, polypeptide, peptide and/or amino acid of human or bovine origin or, more advantageously, free of contaminants of animal origin. In the latter case, the heme source consists of synthetic protoporphyrin IX, the β-NAD and carbohydrate source also being of non-animal origin, the source of vitamins and growth factors being provided by a yeast extract and the gelling substance being agar (a product derived from alga).

Accordingly, the subject of the invention is also a method for producing PRP wherein the solid culture medium and the liquid culture medium are free of contaminants of animal origin.

It has also been sought to optimize the composition of the solid medium so that it is possible to select the bacteria colonies which produce the most PRP. The composition of such a medium should make it possible to obtain:
good individualization of the colonies;
good viability of the colonies;
development and sufficient size of the colonies so as to be able to study their morphology. In order to be able to discriminate between the colonies, it is necessary to have a medium which makes it possible to obtain *Haemophilus influenzae* type b colonies having a sufficient size at the end of 16-24 hours of culture (about 3 to 5 mm).

In one of the preferred embodiments of the method for producing PRP according to the invention, the solid medium comprises:
at least 1 mg/l of β-NAD,
at least 0.5 mg/l of protoporphyrin IX,
a plant peptone and a yeast extract in sufficient quantity for the protein nitrogen concentration in the solid medium to be at least 0.2 g/l and in a proportion such that the ratio of the quantity of plant protein to the quantity of yeast extract in the medium is 0.1 to 9 when the concentration of protein nitrogen of the medium is 0.2 g/l to 0.8 g/l and is 1 to 9 when the concentration of protein nitrogen of the medium is >0.8 g/l,
a carbohydrate,
a detoxifying agent, and
a cocktail of inorganic ions comprising $Na^+$, $K^+$, $Ca^{++}$, $Mg^{++}$, $Fe^{+++}$, $HPO_4^{--}$, $H_2PO_4^-$, $SO_4^{--}$ and $Cl^-$ ions in the form of salt solutions so that the pH of the culture medium is between 6.5 and 7.5, preferably between 7.0 and 7.5.

The carbohydrate used is preferably a sugar of non-animal origin, metabolizable by the bacterium, such as fructose, ribose, xylose, fucose, glycerol, or, in particular, glucose. Good results were obtained with glucose at a concentration of at least 0.1 g/l. Usually, glucose is used at a concentration of 0.1 g/l to 20 g/l and preferably 0.1 g/l to 10 g/l.

The detoxifying agents promote the growth of the bacteria by neutralizing the inhibitory substances that may be present in the agar preparations as reported by Evans N. M et al. (J. Med. Microbiol. Vol 7, pp 305-309, 1974). As detoxifying agent, charcoal, starch, Tween®, polyvinyl alcohol, sodium oleate or sodium dithionite are preferably used. Good results were observed with Tween 80® (polyoxyethylenesorbitan monooleate) used at a concentration of 0.5 to 10 mg/l; a solid medium composition without Tween® produces small size colonies that are indistinguishable from the morphological point of view. One also observes small size colonies indistinguishable from the morphological point of view when the β-NAD concentration is less than 1 mg/l, when the protoporphyrin IX concentration is less than 0.5 mg/l, or when the glucose concentration is less than 0.1 mg/l.

In order to ensure good growth and good viability of the colonies, the quantities of yeast extract and plant peptone are such that the concentration of total protein nitrogen is at least 0.2 g/l. The ratio of the quantity of plant peptone to the quantity of yeast extract in the medium may vary to a large degree, ranging from 0.1 to 9 as long as the concentration of protein nitrogen in the culture medium does not exceed 0.8 g/l. On the other hand, at a higher concentration, there is poor individualization of the colonies due to poor spreading of the bacterial suspension on the solid medium when this ratio is less than 1.

By inoculating this agar-based medium with a heterogeneous population of *Haemophilus influenzae* serotype b bacteria (i.e., which contains both capsulated and noncapsulated bacteria), after 18 to 24 hours of culture white colonies and gray colonies differing in transparency are observed and are distinguishable with the aid of a beam of white light. The white colonies produce more PRP than the gray colonies. Moreover, the white colonies also produce more PRP than the colonies obtained from a charcoal agar-based solid medium supplemented with horse blood (cf. example 2). This medium composition is considered as a selective medium composition because it makes it possible to sort the colonies which produce the most PRP.

According to an even more preferred embodiment of the method according to the invention, the solid medium comprises:
from 5 to 50 mg/l of β-NAD,
from 0.5 to 5 mg/l of protoporphyrin IX,
from 1 to 10 g/l of glucose,
from 1 to 10 mg/l of Tween 80,
from 3 to 4 g/l of $K_2HPO_4$,
from 0.9 to 3 g/l of $KH_2PO_4$,
from 0.5 to 2 g/l of $K_2SO_4$,
from 20 to 500 mg/l of $MgCl_2$,
from 2 to 50 mg/l of $CaCl_2.2H_2O$,
from 1 to 5 mg/l of $FeCl_3.6H_2O$,
from 4 to 8 g/l of NaCl,
from 4 to 8 g/l of a yeast extract, and from 4 to 8 g/l of a garden pea peptone such that the ratio between the quantity of garden pea peptone and the quantity of yeast extract is ≥1 when the protein nitrogen concentration of the medium is >0.8 g/l.

The white colonies obtained from this medium composition produce up to 400 times more PRP than the gray colonies. Their cap locus was studied by digesting the genomic DNA with the aid of the restriction enzymes SmaI and KpnI. Pulsed field electrophoresis was then performed on the digestion product followed by visualization with the aid of a specific PvuII probe according to the operating conditions described in example 3. Surprisingly, all the electrophoretic profiles from white colonies contain an electrophoretic band of 45 kb. No 18 kb electrophoretic band is observed. The cap locus of these colonies consequently contains at least two copies of the 18 kb gene, which means that the bacterial population derived from the white colonies is completely capsulated. On the other hand, the electrophoretic profiles from the gray colonies mainly contain an electrophoretic band of 18 kb. This particularly preferred selective medium composition additionally makes it possible to select white colonies whose bacterial populations are completely capsulated.

In fact, one of the additional means for increasing the yields in the PRP production method that comprises a preliminary phase of culturing on a solid medium consists in transferring into a liquid medium only white colonies that have been obtained from a selective solid medium composition. Preferably, a solid medium composition that makes it possible to obtain white colonies essentially consisting of capsulated bacteria is used.

Accordingly, in a preferred embodiment, the subject of the invention is also a method of producing PRP in which only the white colonies obtained on a selective solid medium composition are transferred into the liquid culture medium.

In a particularly preferred embodiment, these white colonies are transferred into a liquid culture medium that exercises a stabilizing role on the capsulated bacterial population. In addition to the fact that all the culture steps are carried out with media in which the protein nitrogen source is of non-animal origin, or even with media free of contaminants of animal origin notable when synthetic protoporphyrin IX is used, this method also makes it possible to optimize the production of PRP when the *Haemophilus influenzae* serotype b population is heterogeneous and contains capsulated bacteria and noncapsulated bacteria. The step of culture on a solid medium makes it possible to select the white colonies that contain a population of completely capsulated bacteria. The step of amplifying the biomass in the liquid medium stabilizes the population of capsulated bacteria, as seen above, by preventing the development of noncapsulated revertants. The yields of PRP/liter of culture that are finally obtained are then at a maximum (see example 4).

This method can also be used in the production of a population of completely capsulated bacteria. The bacterial population obtained is completely capsulated when the electrophoretic profile of the genomic DNA of this population shows that the cap locus contains at least two copies of the 18 kb gene (cf protocol of example 3) and when the inoculation of an aliquot of this population onto a selective solid medium composition according to the invention produces more than 95% of white colonies, preferably at least 98% of white colonies. After amplification of the bacteria in a stabilizing liquid medium (i.e., one that prevents the appearance of non-capsulated revertant bacteria), the bacterial population obtained is preserved by freeze-drying or by freezing (in this case, a freezing agent of non-animal origin such as glycerol is added to the culture medium). Thus, inoculum batches are made that contain a homogeneous population of completely capsulated bacteria and that offer an additional guarantee of biological safety because they were obtained using culture media that is free of contaminants of animal origin. These inoculum batches can serve in turn to produce PRP.

The subject of the invention is therefore:

A method for producing polyribosyl ribitol phosphate (PRP) wherein all the steps are carried out by means of media free of contaminants of animal origin.

A method for producing a population of completely capsulated *Haemophilus influenzae* serotype b bacteria in which:

(i) *Haemophilus influenzae* serotype b is cultured on a solid medium comprising:
from 5 to 50 mg/l of β-NAD,
from 0.5 to 5 mg/l of protoporphyrin IX,
from 1 to 10 g/l of glucose,
from 1 to 10 mg/l of Tween 80,
from 3 to 4 g/l of $K_2HPO_4$,
from 0.9 to 3 g/l of $KH_2PO_4$,
from 0.5 to 2 g/l of $K_2SO_4$,
from 20 to 500 mg/l of $MgCl_2$,
from 2 to 50 mg/l of $CaCl_2.2H_2O$,
from 1 to 5 mg/l of $FeCl_3.6H_2O$,
from 4 to 8 g/l of NaCl,
from 4 to 8 g/l of a yeast extract, and
from 4 to 8 g/l of a garden pea peptone such that the ratio between the quantity of garden pea peptone and the quantity of yeast extract is ≥1 when the protein nitrogen concentration of the medium is >0.8 g/l, and (ii) one or more white colonies obtained in (i) are transferred into and cultured in a liquid culture medium comprising:
from 0.1 mg/l to 5 mg/l of protoporphyrin IX,
from 2 to 50 mg/l of β-NAD,
from 2 to 20 g/l of glucose,
from 2 to 5 g/l of a yeast extract,
a garden pea peptone equivalent to a protein nitrogen concentration of 0.4 g/l to 1.5 g/l, and
a cocktail of inorganic ions: $Na^+$, $NH_4^+$, $Ca^{++}$, $Mg^{++}$, $HPO_4^-$, $H_2PO_4^-$, $SO_4^{--}$ and $Cl^-$ in the form of salt solutions so that the pH of the medium is between 6.5 and 7.5, preferably between 7.0 and 7.5, and (iii) the bacterial culture obtained in (ii) is frozen or freeze-dried.

A method for producing a population of completely capsulated *Haemophilus influenzae* serotype b bacteria wherein all the steps are carried out by means of media free of contaminants of animal origin.

The subject of the invention is also the use of a homogeneous population of capsulated *Haemophilus influenzae* serotype b bacteria obtained according to this method, for the production of PRP.

The subject of the invention is a vaccine against *Haemophilus influenzae* type b meningitis comprising PRP obtained from one of the embodiments of the method according to the invention.

The subject of the invention is finally a solid culture medium for *Haemophilus influenzae* serotype b comprising:
at least 1 mg/l of β-NAD,
at least 0.5 mg/l of protoporphyrin IX,
a plant peptone and a yeast extract in a sufficient quantity for the protein nitrogen concentration in the medium to be at least 0.2 g/l of protein nitrogen and in a proportion such that the ratio between the quantity of plant peptone and the quantity of yeast extract in the medium is 0.1 to 9 when the protein nitrogen concentration of the medium is 0.2 g/l to 0.8 g/l and is 1 to 9 when the protein nitrogen concentration of the medium is >0.8 g/l, a carbohydrate, a detoxifying agent, and a cocktail of inorganic ions: $Na^+$, $K^+$, $Ca^{++}$, $Mg^{++}$, $Fe^{+++}$, $HPO_4^{--}$, $H_2PO4^-$, $SO_4^{--}$ and $Cl^-$ in the form of salt solutions such that the pH of the medium is between 6.5 and 7.5, preferably between 7.0 and 7.5.

Preferably, the solid culture medium comprises:

from 5 to 50 mg/l of β-NAD, from 0.5 to 5 mg/l of protoporphyrin IX, from 1 to 10 g/l of glucose, from 1 to 10 mg/l of Tween 80, from 3 to 4 g/l of $K_2HPO_4$, from 0.9 to 3 g/l of $KH_2PO_4$, from 0.5 to 2 g/l of $K_2SO_4$, from 20 to 500 mg/l of $MgCl_2$, from 2 to 50 mg/l of $CaCl_2.2H_2O$, from 1 to 5 mg/l of $FeCl_3.6H_2O$, from 4 to 8 g/l of NaCl, from 4 to 8 g/l of a yeast extract, and from 4 to 8 g/l of a garden pea peptone such that the ratio between the quantity of garden pea peptone and the quantity of yeast extract is ≥1 when the protein nitrogen concentration of the medium is >0.8 g/l.

The present invention will be understood more clearly in the light of the following examples which serve to illustrate the invention without as a result limiting the content thereof.

Example 1

Influence of Protoporphyrin IX on the Production of PRP in a Plant Peptone-based Culture Medium 1) Methodology The production of PRP obtained after 16 hours of bacterial culture in liquid plant peptones-based culture media in which the heme source was either hemin or protoporphyrin IX of animal origin (porcine protoporphyrin) in disodium salt form, or protoporphyrin IX of purely synthetic origin in disodium salt form was compared. The hemin and protoporphyrin IX concentration ranges in the culture media varied from about 0.010 g/l to about 2 g/l so as to obtain PRP titration curves as a function of the heme source tested and as a function of the plant peptone tested. An enzymatic hydrolysate of garden pea peptone provided by Kerry (Hy pea 7404) and a wheat peptone provided by Organotechnie (19559) were tested at a concentration in the culture medium equivalent to 0.87 g/l of protein nitrogen. By reference to the current methods for the production of PRP, PRP production was also measured in a medium that contains a peptone of animal origin, such as casein hydrolysate (HAC) provided by Solabia at a concentration in the medium equivalent to 0.87 g/l with increased concentrations of hemin (see table III).

1.1) Preparation of the Media 1.1.1. Stock solution of β-NAD (Fluka) at 1 g/l in water which was ultrafiltered and then sterilized by filtration through 0.22 μm.

1.1.2. Stock solution of hemin (Sigma) at 0.25 g/l in water was ultrafiltered, comprising 5 ml of 25% aqueous ammonia (Cooper) to aid dissolution. The stock solution was sterilized by filtration through 0.22 μm.

1.1.3. Stock solution of porcine protoporphyrin IX (Sigma) at 0.25 g/l in ultrafiltered water comprising 5 ml of 25% aqueous ammonia (Cooper) in order to facilitate the dissolution. The stock solution was sterilized by filtration through 0.22 μm.

1.1.4. Stock solution of synthetic protoporphyrin IX at 0.25 g/l in ultrafiltered water comprising 5 ml of 25% aqueous ammonia (Cooper) in order to facilitate the dissolution. The stock solution was also heated to 80° C. in a water bath with stirring in order to complete the dissolution before being sterilized by filtration through 0.22 μm. The protoporphyrin IX, in disodium salt form, was synthesized according to the method described in the U.S. provisional patent application Ser. No. 12/057,574, filed Mar. 28, 2008 and application Ser. No. 60/943,735 and filed on Jun. 13, 2007 using the steps which are described in scheme 2.

The stock solutions of hemin and protoporphyrin IX were checked for their respective contents of active compounds after sterilizing filtration. The protoporphyrin IX and hemin contents were determined by Reversed Phase High Performance Liquid Chromatography (RP-HPLC). The chromatographic chain comprises a twin head pump module allowing the formation of a binary gradient, a programmable automatic injector, a diode array UV detector and a chromatographic column of the type Synergi 4 μm, Polar RP-80A (150×4.6) mm, ref 00F-4336-E0, Phenomenex.

The stock solution of hemin (Sigma) to be checked after filtration was diluted ⅓ in distilled water. The stock solutions of porcine protoporphyrin IX (Sigma) and of synthetic protoporphyrin IX to be checked after filtration were diluted ¼ in distilled water. In parallel, a calibration series was prepared in ammoniated water ranging from 0.025 g/l to 0.125 g/l of protoporphyrin IX from porcine protoporphyrin IX from Sigma (ref: 25838-5) and a calibration series ranging from 0.050 g/l to 0.150 g/l of hemin from hemin from Sigma (ref: H5533-256). The samples to be checked and the various solutions of the calibration series were injected in a volume of 20 μl (for the hemin solutions and samples) and of 5 μl (for the protoporphyrin IX solutions and samples). The initial mobile phase consisting of a volume for volume mixture of acetonitrile and 10 mM KH2PO4 pH 2.5 is set at a flow rate of 1 ml/min. A discontinuous gradient was then produced from this mobile phase in order to separate the molecules of interest which are detected at a wavelength of 400 nm. After having established the calibration series and on the basis of the surface area of the peaks for the samples to be checked, the hemin and protoporphyrin IX concentrations in the various filtered stock solutions were deduced therefrom which were 0.295 g/l for the hemin solution, 0.187 g/l for the porcine protoporphyrin IX solution and 0.249 g/l for the synthetic protoporphyrin IX solution, respectively. These concentrations were not subsequently adjusted to the target concentration of 0.250 g/l but these concentrations really present in the stock solutions of hemin and protoporphyrin IX were used in the analysis of the results.

1.1.5. Stock solution of autolytic yeast extract (Solabia) at 125 g/l in water which was ultrafiltered and then sterilized through 0.22 μm.

1.1.6. Stock solution of glucose at 465.12 g/l in water which was ultrafiltered and then sterilized by filtration through 0.22 μm.

1.1.7. Enrichment solution
   It consisted of 40 ml of stock solution of yeast extract, 43 ml of stock solution of glucose and 5 ml of stock solution of β-NAD.
1.1.8. Basal medium
   Wheat plant peptone (Organotechnie-Ref 19559) or garden pea plant peptone (Kerry-Ref Hypea 7404) in a sufficient quantity to provide the equivalent of 0.95 g of protein nitrogen per liter of basal medium, the quantity of protein nitrogen being assayed according to the kjedhal method,
   50% sodium lactate in 50% aqueous solution (VWR): 1.8 ml,
   disodium hydrogen phosphate·12H$_2$O (Budenheim): 31.14 g,
   sodium dihydrogen phosphate·2H$_2$O (Merck): 2.03 g,
   L-cystine (Jera France): 0.07 g,
   37% HCl (VWR): 0.07 ml,
   L-tryptophan (Jera France): 0.02 g,
   ammonium sulfate: 1 g,
   magnesium sulfate·7H$_2$O: 0.4 g,
   calcium chloride·2H$_2$O: 0.02 g/l,
   ultrafiltered water: sufficient quantity for 1 liter.
   The basal medium was finally sterilized using an autoclave at 121° C. for 30 minutes.
1.2) Operating Protocol The culture was performed in 500 ml Erlenmeyer flasks. Into each Erlenmeyer flask, there were introduced 100 ml of basal medium containing either wheat peptone, or garden pea peptone, 8.8 ml of enrichment medium and a variable volume of stock solution of hemin, of porcine protoporphyrin IX or of synthetic protoporpyrin IX such that the theoretical concentrations of hemin (or of protoporphyrin IX) tested in the various culture media were between 10 µg/l and about 2000 µg/l (see tables I and II). Each Erlenmeyer flask is inoculated with the contents of a frozen product of *Haemophilus influenzae* serotype b which contains $10^8$ to $10^{10}$ bacteria/ml at an inoculation rate of 0.2% (V/V). After 16 hours of incubation with stirring at 175 rpm in an incubator at 37° C., the OD of the bacterial suspension obtained and the PRP concentration were measured in each Erlenmeyer flask by collecting a small amount of culture supernatant.

1.3) Assay of PRP

The PRP productivity was determined on the basis of a sandwich-type ELISA assay in duplicate on the culture supernatants.

The ELISA microplates were sensitized overnight at +4° C. by introducing into each well 100 µl of a solution of immunosera from rabbits hyperimmunized with *Haemophilus influenzae* type b microbes, which solution is diluted beforehand in a 0.2M carbonate buffer pH 9.6 (dilution≈1/2000). After rinsing and saturation of the ELISA microplates, a calibration series was produced in each microplate from a purified solution of PRP at 1 mg/ml in distilled water by producing successive dilutions in a dilution buffer (PBS/0.05% Tween 20/1% bovine serum albumin). The culture supernatants to be assayed were also introduced by also carrying out successive dilutions in the dilution buffer. After another incubation of about 2 hours at 37° C., followed by a phase for rinsing of the microplates, there were introduced into the microwells 100 µL of a solution of biotinylated rabbit antibodies obtained by treating the sera of rabbits vaccinated with the *Haemophilus influenzae* type b vaccine conjugated with the tetanus protein with a biotinylation agent, diluted beforehand in the dilution buffer (dilution≈1/500). After incubation for 1 hour at 37° C. followed by a rinsing step, there was added to each of the microwells 100 µl of a solution of streptavidin coupled with peroxidase (Southern Biotechnology—ref 7100-05) diluted beforehand in the dilution buffer (dilution≈1/5000). After incubation for 1 hour at 37° C. followed by a rinsing step, there was added to each microwell 100 µl of a visualization solution (solution of ortho-phenylenediamine at 0.4 mg/ml in 0.05M phosphate-citrate buffer, pH=5, supplemented with 0.3 µl of hydrogen peroxide at 0.03%). After a visualization time of 20 minutes protected from light, the reaction was blocked by adding 50 µl/well of 2N H2SO4. The microplates were read at 492 and 620 nm (in order to take into account the absorption of the plastic). From the optical density values obtained on the samples tested, the PRP content in the various culture supernatants was determined by interpolation by means of the calibration series.

1.4) Results

The results are represented in tables 1 and 2 below and in FIGS. 1 and 2.

TABLE 1

| Garden pea + porcine protoporphyrin IX | | | | |
|---|---|---|---|---|
| Porcine protoporphyrin IX in µg/l | PRP in mg/l Assay 1 | PRP in mg/l Assay 2 | Mean PRP in mg/l | Standard deviation PRP |
| 7.48 | 15.1 | 16.1 | 15.6 | 0.71 |
| 37.4 | 143 | 149 | 146 | 4.24 |
| 74.8 | 344 | 354 | 349 | 7.07 |
| 187 | 450 | 490 | 470 | 28.28 |
| 374 | 415 | 432 | 423.5 | 12.02 |
| 748 | 495 | 523 | 509 | 19.80 |
| 1122 | 492 | 550 | 521 | 41.01 |
| 1496 | 466 | 493 | 479 | 19.09 |
| Garden pea + synthetic protoporphyrin IX | | | | |
| Synthetic protoporphyrin IX in µg/l | PRP in mg/l Assay 1 | PRP in mg/l Assay 2 | Mean PRP in mg/l | Standard deviation PRP |
| 9.96 | 11.3 | 11.8 | 11.55 | 0.35 |
| 49.8 | 139 | 134 | 136.5 | 3.54 |
| 99.6 | 330 | 383 | 356.5 | 37.48 |
| 249 | 474 | 502 | 488 | 19.80 |
| 498 | 383 | 392 | 387.5 | 6.36 |
| 996 | 524 | 474 | 499 | 35.36 |
| 1494 | 503 | 523 | 513 | 14.14 |
| 1992 | 480 | 497 | 488.5 | 12.02 |
| Garden pea + hemin | | | | |
| Hemin in µg/l | PRP in mg/l Assay 1 | PRP in mg/l Assay 2 | Mean PRP in mg/l | Standard deviation PRP |
| 11.8 | 3.82 | 3.79 | 4 | 0.02 |
| 59 | 7.61 | 7.13 | 7 | 0.34 |
| 118 | 23.4 | 17.5 | 20 | 4.17 |
| 295 | 51.2 | 45.4 | 48 | 4.10 |
| 590 | 95.4 | 72.9 | 84 | 15.91 |
| 1180 | 234 | 232 | 233 | 1.41 |
| 1770 | 209 | 211 | 210 | 1.41 |
| 2360 | 505 | 482 | 494 | 16.26 |
| 3540 | 129 | 154 | 142 | 17.68 |

TABLE 2

| Wheat + porcine protoporphyrin IX | | | | |
|---|---|---|---|---|
| Porcine protoporphyrin IX in µg/l | PRP in mg/l Assay 1 | PRP in mg/l Assay 2 | Mean PRP in mg/l | Standard deviation PRP |
| 7.48 | 25.5 | 28.3 | 26.9 | 1.98 |
| 37.4 | 136 | 149 | 142.5 | 9.19 |

TABLE 2-continued

| | | | | |
|---|---|---|---|---|
| 74.8 | 429 | 299 | 364 | 91.92 |
| 187 | 452 | 408 | 430 | 31.11 |
| 374 | 397 | 374 | 385.5 | 16.26 |
| 748 | 399 | 377 | 388 | 15.56 |
| 1122 | 446 | 329 | 387.5 | 82.73 |
| 1496 | 464 | 283 | 373.5 | 127.9 |

| Wheat + synthetic protoporphyrin IX | | | | |
|---|---|---|---|---|
| Synthetic protoporphyrin IX in µg/l | PRP in mg/l Assay 1 | PRP in mg/l Assay 2 | Mean PRP in mg/l | Standard deviation PRP |
| 9.96 | 33.5 | 27.9 | 30.7 | 3.96 |
| 49.8 | 317 | 319 | 318 | 1.41 |
| 99.6 | 389 | 437 | 413 | 33.94 |
| 249 | 345 | 350 | 347.5 | 3.54 |
| 498 | 380 | 409 | 394.5 | 20.51 |
| 996 | 401 | 404 | 402.5 | 2.12 |
| 1494 | 358 | 350 | 354 | 5.66 |
| 1992 | 378 | 430 | 404 | 36.77 |

| Wheat + hemin | | | | |
|---|---|---|---|---|
| Hemin in µg/l | PRP in mg/l Assay 1 | PRP in mg/l Assay 2 | Mean PRP in mg/l | Standard deviation PRP |
| 11.8 | 4.98 | 5.61 | 5.3 | 0.45 |
| 59 | 13 | 13.7 | 13.35 | 0.49 |
| 118 | 17.7 | 17.5 | 17.60 | 0.14 |
| 295 | 35.3 | 30.2 | 32.75 | 3.61 |
| 590 | 71.4 | 73.4 | 72.4 | 1.41 |
| 1180 | 327 | 256 | 291.5 | 50.2 |
| 1770 | 487 | 446 | 466.5 | 28.99 |
| 2360 | 487 | 504 | 495.5 | 12.02 |

TABLE 3

| HAC + Hemin | | | | |
|---|---|---|---|---|
| Hemin in µg/l | PRP in mg/l Assay 1 | PRP in mg/l Assay 2 | Mean PRP in mg/l | Standard deviation PRP |
| 11.8 | 18.9 | 14.7 | 16.8 | 2.97 |
| 59 | 82.7 | 77.7 | 80.2 | 3.54 |
| 118 | 183 | 216 | 199.5 | 23.33 |
| 295 | 325 | 304 | 314.5 | 14.85 |
| 590 | 381 | 440 | 410.5 | 41.72 |
| 1180 | 424 | 405 | 414.5 | 13.44 |
| 1770 | 404 | 519 | 461.5 | 81.32 |
| 2360 | 439 | 490 | 464.5 | 36.06 |

FIG. 1 is a reproduction of the results in table I and shows the PRP production curves obtained as a function of the concentration and source of heme used in a medium which contains garden pea peptones. The PRP production curves are equivalent depending on whether a synthetic protoporphyrin IX or a protoporphyrin IX of animal origin is used as source of heme. On the other hand, the production of PRP is substantially lower when the medium contains hemin compared with a medium which contains protoporphyrin IX, this being in the entire concentration range tested. Only about 200 µg/l of protoporphyrin IX have to be used in order to have an optimum PRP production (≈480 mg/ml) while about 2500 µg/l of hemin are required in order to have a maximum production of PRP. About 12.5 times less protoporphyrin IX than hemin is therefore required in a culture medium based on garden pea peptone in order to have a maximum production of PRP.

Figure 2:
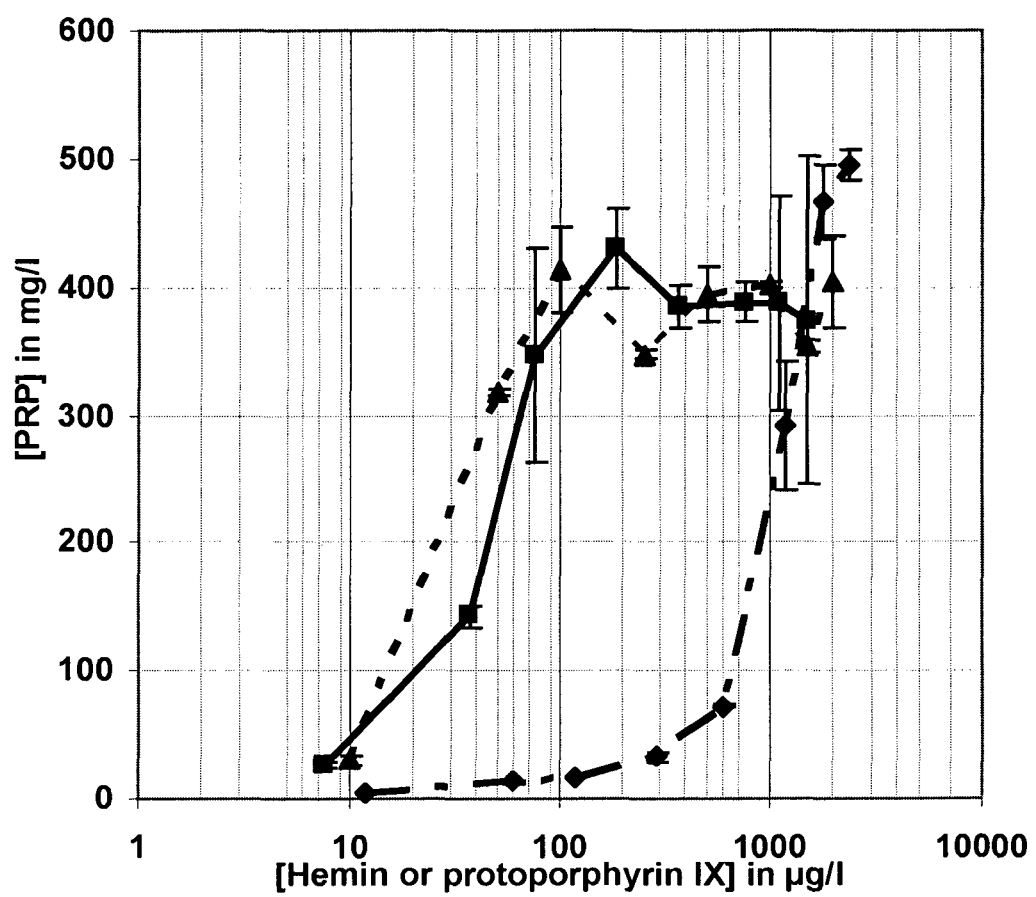

FIG. 2 is a reproduction of the results in table II and shows the PRP production curves obtained as a function of the concentration and source of heme used in a medium which contains wheat peptones. The PRP production curves are equivalent depending on whether a synthetic protoporphyrin IX or a protoporphyrin IX of animal origin is used as source of heme. On the other hand, the production of PRP is lower when the medium contains hemin compared with a medium which contains protoporphyrin IX at equivalent concentrations, and the lower the hemin concentration the more clearly this appears. Only about 100 µg/l of protoporphyrin IX have to be used in order to have an optimum PRP production (≈400 mg/ml) while about 1500 µg/l of hemin are required in order to have an equivalent production of PRP. About 15 times less protoporphyrin IX than hemin is therefore required in a culture medium based on wheat peptone in order to have a maximum production of PRP.

The results in Table I, II and III also show that the hemin concentration in an animal peptone and hemin-based medium, which is nevertheless the medium composition recommended for producing PRP, shall be two to five times more important than the protoporphyrin IX concentration required in a vegetal peptone-based medium, such as garden pea peptone or wheat peptone to get the same PRP concentration in culture supernatant. For example, to obtain a concentration of about 400 mg/l of PRP in a casein hydrolysate and hemin-based medium, the hemin concentration shall be at least 500 µg/l, while a concentration of about 100 µg/l of protoporphyrin IX is enough in a wheat peptone or garden pea peptone and protoporphyrin IX-based medium. Therefore, Media made of vegetal peptone and protoporphyrin IX appear to be more convenient than the current media made of animal peptone and hemin used for the production of PRP.

Example 2

Influence of the Composition of the Solid Medium on the Production of PRP by the Colonies A freeze-dried material of a homogeneous population of Haemophilus influenzae serotype b bacteria containing about $10^8$ microbes was taken up in 1 ml of Dulbecco PBS buffer (Gibco ref 14040-083). Ten-fold serial dilutions were carried out in this buffer. 50 µl of each of the dilutions: $10^{-5}$, $10^{-6}$ and $10^{-7}$, were collected and inoculated either on Petri dishes containing various selective solid media compositions according to the invention, or on a Petri dish containing a standard solid medium containing a charcoal agar (Difco, Ref 289410) supplemented with 10% (v/v) defibrinated boiled horse blood (BioMérieux, Ref 55832).

After incubating overnight at 37° C. in an incubator containing 10% $CO_2$, the colonies were examined by transparency, under a 75 W lamp, the Petri dishes being closed. The colonies appeared opaque and uniform on the standard medium. On the other hand, white colonies and gray colonies were observed on the selective media. Four colonies were randomly collected from the standard solid medium and 4 gray colonies and 4 white colonies from two of the selective media tested (A and B) whose compositions per liter were as follows:

| | Selective medium A | Selective medium B |
|---|---|---|
| β-NAD: | 10 mg | 10 mg |
| Protoporphyrin IX: | 5 mg | 0.5 mg |
| Glucose: | 1 g | 1 g |

-continued

|  | Selective medium A | Selective medium B |
|---|---|---|
| Tween 80: | 1 mg | 1 mg |
| $K_2HPO_4$: | 3 g | 3 g |
| $KH_2PO_4$: | 0.94 g | 0.94 g |
| $K_2SO_4$ | 0.5 g | 0.5 g |
| $MgCl_2$: | 0.5 g | 0.5 g |
| $CaCl_2 \cdot 2H_2O$: | 0.002 g | 0.002 g |
| $FeCl_3 \cdot 6H_2O$: | 0.005 g | 0.005 g |
| NaCl: | 8 g | 8 g |
| Yeast extract (Difco-ref: 212 740): | 5 g | 5 g |
| Garden pea peptone in acid hydrolysate form (Oxoid): | 5.3 g | 5.3 g |
| Bacto agar: | 15 g | 15 g |

On each colony collected, the PRP content was assayed by High Performance Chromatography coupled with pulsed field amperometric detection (HPAEC/PAD) chromatography.

The quantification of PRP was carried out by assaying ribitol which is one of the components of the repeating unit of the polysaccharide and which is quantitatively released after acid hydrolysis.

2.1) Preparation of the Samples

Each colony was taken up in 500 µl of ultrafiltered water and then 100 µl of the suspension was collected and diluted in 300 µl of ultrafiltered water.

2.2) Preparation of the Calibration Series

Starting with a ribitol stock solution at 1 mg/l in ultrafiltered purified water, a ribitol calibration series was prepared ranging from 0 to 20 µg/ml. The final volume of each sample of the calibration series was also 400 µl.

2.3) Acid Hydrolysis

100 µl of a 10 N trifluoroacetic acid solution was added to each sample preparation or to each sample of the calibration series. The hydrolysis was performed for 2 hours at 120° C. All the tubes were then dried under a nitrogen stream and each dried material was taken up in 400 µl of ultrafiltered purified water at the time of the analysis.

2.4) Analysis by HPAEC-PAD Chromatography

100 µl of each of the hydrolysates were injected onto an analytical column CARBOPAC MA1 (4×250 mm) (DIONEX #44066) equilibrated beforehand with a 480 nM sodium hydroxide solution. The column was subjected to a stream of a solution containing 48% of 1M sodium hydroxide and 52% of a solution of ultrafiltered purified water for 40 minutes at a flow rate of 0.4 ml/min in order to elute the two constituent monosaccharides of PRP. The temperature of the column was maintained at 30° C. for the entire duration of the analysis. The monosaccharides were detected with the aid of an ED40 multimode electrochemical detector coupled with an amperometric cell (DIONEX #44094).

Under these conditions, the chromatography peak corresponding to the ribitol released during the hydrolysis of PRP appeared at 19±5% min.

The calibration curve (quantity of ribitol as a function of the surface area of the chromatographic peaks) was established from the calibration series and then the quantity of ribitol contained in each of the sample preparations was determined by interpolation. The quantity of PRP which each sample contains was deduced therefrom followed by the PRP concentration in each colony knowing that ribitol represents 41% of the weight of PRP.

2.5) Determination of the Biomass of the Colonies

The protein content of each colony determined according to the MicroBCA method (Pierce) reflected the biomass of each colony. For that, the colonies were individually collected and then taken up in 200 µl of sterile ultrafiltered water. The mixture was stirred on a vortex for 30 seconds. Samples (10 µl to 40 µl) were collected in order to carry out the protein assay with the aid of the MicroBCA kit (Pierce) according to the manufacturer's recommendations. A calibration series was prepared from 100 µg/ml bovine albumin serum. The samples and the calibration series were read on a spectrophotometer at 562 nm. The protein concentrations of the samples, expressed in µg/colony, were calculated with the aid of the calibration series.

2.6) Results

The results expressed in µg of PRP per unit of protein mass (expressed in µg) are reported in the table below.

|  |  |  | Charcoal agar | Selective medium A | Selective medium B |
|---|---|---|---|---|---|
| Colony morphology | opaque | C1 | 0.030* |  |  |
|  |  | C2 | 0.031 |  |  |
|  |  | C3 | 0.025 |  |  |
|  |  | C4 | 0.024 |  |  |
|  | gray | C1 |  | 0.000 | N.D |
|  |  | C2 |  | 0.012 | 0.000 |
|  |  | C3 |  | 0.018 | 0.000 |
|  |  | C4 |  | 0.000 | 0.000 |
|  | white | C1 |  | 0.082 | 0.151 |
|  |  | C2 |  | 0.079 | 0.078 |
|  |  | C3 |  | 0.079 | 0.176 |
|  |  | C4 |  | 0.122 | 0.150 |

*represents the quantity of PRP (in µg) produced by a colony expressed relative to its protein mass unit (in µg).
N.D.: not assayed The production of PRP by the colonies is higher, the higher the quantity of PRP assayed per unit of protein mass. These results show that the production of PRP by the white colonies is 3 to 5 times higher than the production of the colonies collected from charcoal agar. On the other hand, the gray colonies generally produce lower quantities of PRP than the colonies collected from charcoal agar.

Example 3

Influence of the Step of Culture on Selective Solid Medium on the Production of PRP in Liquid Medium Two methods for producing PRP were compared. In the first method, the contents of a frozen material (=108 bacteria/ml) of a population of *Haemophilus influenzae* type b bacteria, called stock population, was directly inoculated into a liquid culture medium according to the invention. The characteristics of the stock population were analyzed beforehand (see next paragraph). In the second protocol, a daughter population was derived from the stock population using a selective solid medium according to the invention which made it possible to select a daughter population from the white colonies which contain 100% of capsulated bacteria. The daughter population was then inoculated into the same culture medium as the stock population. The production of PRP by the stock population and the daughter population were then measured and compared in a third step.

3.1) Characteristics of the Stock Population 3.1.1: Analysis of the cap locus 3.1.1.1: Reagents Bacterial Lysis Buffers Pett IV buffer: 10 mM Tris-HCl pH 7.4, 1M NaCl 1× lysis solution: 6 mM Tris-HCL pH 7.4, 1M NaCl, 10 mM EDTA, 0.5% Brij 58, 0.2% sarkosyl, 5 mg/ml lysozyme, 1 µg/ml Rnase ESP solution: 10 mM Tris-HCL pH 7.4, 1 mM EDTA, 1% SDS, 1 mg/ml proteinase TE solution: 10 mM Tris-HCl pH 7.4, 0.1 mM EDTA Enzymatic Digestion SmaI: (GIBCO-BRL Ref: 15228-018)

10× digestion buffer 4: (GIBCO BRL, supplied with the enzyme)—to be diluted 10 fold in sterile purified water free of nuclease at the time of use KnI: (INVITROGEN Ref: 155232-036)

10× digestion buffer 4: (INVITROGEN Ref: 155232-036)—to be diluted 10 fold in sterile purified water free of nuclease at the time of use Pulsed Field Electrophoresis Buffer 10×TBE buffer: 890 mM Tris-HCL pH 7.4, 890 mM boric acid, 250 mM EDTA pH 8.0—to be diluted 20 fold in ultrafiltered water at the time of use PvuII Probe Labeled with Digoxigenin:

The specific labeled PvuII probe was obtained from a DNA preparation obtained from the plasmid pBR322-pU038 (Department of Pediatrics—University of Oxford—John Radcliffe Hospital). 20 µg of plasmid DNA were digested for 2 hours at 37° C. in the presence of 40 units of enzyme pvuII (NEBIOLABS Ref. #R0151-S) in a 10× buffer 4 (NEBIOLABS Ref. #B7002-S) diluted 10 fold beforehand in sterile water free of nuclease. The digestion product was then subjected to electrophoresis on agarose gel at 1% weight/volume in the presence of a 1×TAE buffer to which 0.25% volume/volume of bromophenol blue, 0.25% volume/volume of xylene cyanol FF, and 30% volume/volume of glycerol have been added. The 2.1 kb band of interest corresponding to the PvuII DNA fragment was collected at the end of the migration. The DNA was then extracted from the agarose gel by passing over a "Nucleospin" column (Macherey-Nalgel Ref: 740590.250) and then its integrity was checked by spectrophotometric reading at 260 nm. Finally, the PvuII probe was labeled with digoxigenin using the labeling kit "DIG-Chem-Link Labeling and Detection Set" (ROCHE Ref: 1836463).

The labeled probe was stored at −20° C.

3.1.1.2: Operating protocol

Figure 3:
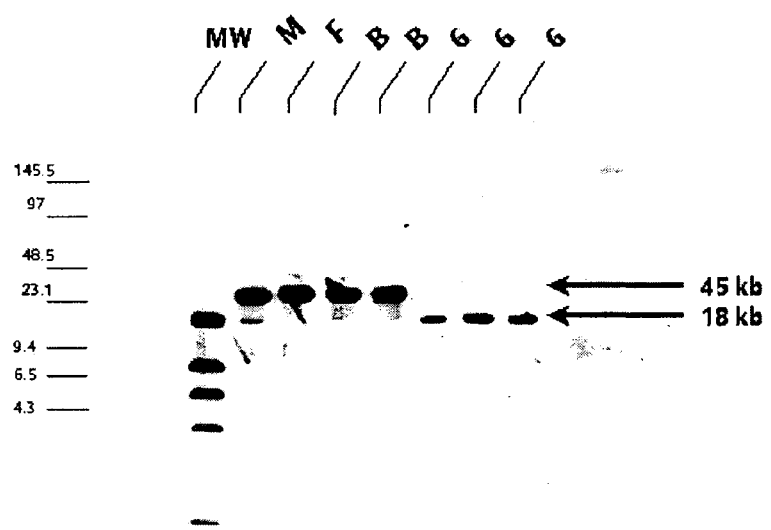

An ampoule of the stock population was thawed and inoculated onto a Petri dish containing a standard solid medium consisting of charcoal agar (Difco, ref 289410) supplemented with 10% (v/v) defibrinated boiled horse blood (BioMérieux, ref 55832). After incubating for 18 h at 37° in an incubator containing 10% $CO_2$, the colonies obtained were harvested and suspended in a Pett IV buffer so that the OD 680 nm is ≈1.8. The bacterial suspension was mixed volume for volume with low-melting point agarose at 2% (v/v) (Ref: BioRad, ref 162-0138), tempered at 50° C. and then this mixture was distributed in plug molds (BioRad Ref: 170-3713) in an amount of ≈80 µl/plug. Agarose molds containing the whole microbe were thus obtained. Each plug was placed in 1 ml of 1× lysis solution. After incubating for 6 h at 37° C., this solution was replaced with 1 ml of an ESP solution. After another incubation overnight at 50° C., each plug was washed 3 times with 4 ml of a TE solution for 30 min. The genomic DNA of the lysed bacteria which was contained in each plug was then digested overnight at 25° C. with the aid of 300 µl of a 1× digestion buffer 4 (GIBCO BRL) containing 20 units of enzyme SmaI (GIBCO-BRL Ref: 15228-018) and then washed with 4 ml of a TE solution. The digestion was continued for 7 hours at 30° C. with the aid of 200 µl of a 1× buffer 4 (INVITROGEN Ref: 155232-036) containing 20 units of the enzyme KpnI (INVITROGEN ref: 155232-036) followed by washing in a TE solution. These two restriction enzymes released the cap locus of the bacterial genomic DNA. The digested plugs were inserted into a certified agarose gel at 0.8% v/v (BIORAD ref: 162-0138) and then subjected to pulsed field electrophoresis carried out in a 0.5×TBE buffer for 13 hours, using an apparatus of the "Chef mapper" type (Biorad) set so that 6 volt/cm, an angle of 120°, a linear progression, an initial switch time of 0.9 s and a final switch time of 11.54 seconds were applied. The gel was transferred to a positively charged nylon filter (Roche Ref: 1209272) by semidry transfer with the aid of the apparatus "Vacugene XL Vacuum blotting System" (Pharmacia) according to the manufacturer's recommendations. The DNA transferred onto the nylon filter was fixed with UV for 3 min at 312 nm. The filter was then prehybridized for 2 hours at 42° C. in "DIG easy hyb" buffer (Roche ref: 1585738), and then hybridized overnight at 42° C. in "DIG easy hyb" buffer containing 20-50 ng of a specific PvuII probe labeled with digoxigenin/ml of buffer. This probe specifically recognized the *Haemophilus influenzae* serotype b cap locus. The filter was then washed twice with the aid of a low "stringency" buffer at 65° C. followed by washing in a high "stringency" buffer. The filter was then visualized with the aid of a luminescent substrate (CDP-star: Roche Ref: 2041677) after having added a solution of alkaline phosphatase-labeled antidigoxigenin antibodies using the kit "Dig-Chem-link labeling and detection Set" (Roche). The electrophoretic profile obtained was represented in FIG. 3. Two bands of 18 kb and 45 kb were observed, which indicated that the structure of the cap locus of the stock population was heterogeneous. A portion of the population possessed a cap locus which contains two copies of the 18 kb gene, corresponding to the electrophoretic band of 45 kb, while the other portion possessed a cap locus in a nonduplicated form, corresponding to the electrophoretic band of 18 kb. Consequently, the stock population was a mixture of capsulated and noncapsulated bacteria. This heterogeneity was moreover confirmed using the test for determining the percentage of white colonies obtained after inoculation of the stock population onto a selective solid medium (see example 2).

3.2) Culture of the Stock Population on Selective Solid Medium: Determination of the Percentage of Bacteria Forming White Colonies on Selective Solid Medium and Deriving of a Daughter Population Essentially Consisting of Capsulated Bacteria.

3.2.1) Determination of the percentage of bacteria forming white colonies.

The step of culturing on a selective solid medium and the morphological analysis of the colonies obtained were carried out according to the same operating conditions described in example 2. The composition of the selective solid medium corresponded to that of the selective medium A of example 2.

The number of white colonies per 100 colonies visualized was determined. 60% of the colonies were in the form of white colonies, which indeed confirmed that the initial stock population was heterogeneous and contained a mixture of capsulated and noncapsulated bacteria.

3.2.2) Selection and Characterization of the Daughter Population 3.2.2.1) Selection of the daughter population A white colony which was obtained after 18 to 24 hours of culture on the selective solid medium A was inoculated into a tube containing 2 ml of a composition of liquid medium identical to the selective solid medium without Bacto agar. After another incubation of 20 hours at 37° C., with shaking, the contents of the tube were transferred into an Erlenmeyer flask containing 50 ml of a liquid medium according to the invention whose composition per liter was as follows:

β-NAD: 5 mg
protoporphyrin IX: 1 mg
glucose: 20 g
yeast extract: 5 g
garden pea peptone (Hypea 7404 (Quest)): 7.42 g
sodium lactate in 60% aqueous solution: 1.49 ml
cystine: 0.07 g
tryptophan: 0.02 g
$Na_2HPO_4.12H_2O$: 31.14 g
$NaH_2PO_4.2H_2O$: 2.03 g
$(NH_4)_2SO_4$: 1 g
$MgSO_4.7H_2O$: 0.4 g
$CaCl_2.2H_2O$: 0.02 g The Erlenmeyer flask was placed in an incubator at 37° C., with shaking. When the OD at 600 nm was close to 2, a volume of glycerol is added such that its final concentration in the bacterial suspension is 20% (v/v). The bacterial suspension was distributed into Nunc tubes in 1 ml before being frozen at −70° C. A daughter bacterial population was thus derived in the form of frozen materials, produced from a white colony obtained on a composition of selective solid medium and which was derived from a bacterium of the stock population.

3.2.2.2) Characterization of the daughter bacterial population

The analysis of the cap locus of the daughter population was carried out according to the protocol described in paragraph 3.1.1.2. The electrophoretic profile showed a single band of 45 kb, which indicates that the cap locus of the daughter population is essentially in a duplicated form of the 18 kb gene (cf FIG. 3). Consequently, the daughter bacterial population essentially consisted of capsulated bacteria. The homogeneity of this population was confirmed by the fact that it also produces 100% of white colonies when it was inoculated onto a selective solid medium.

3.3) Comparison of the Production of PRP by the Bacteria of the Stock Population and of the Daughter Population The contents of an ampoule containing ≈$10^{10}$ bacteria obtained either from the stock population, or from the daughter population, were directly inoculated into an Erlenmeyer flask containing 200 ml of a liquid medium whose composition was that indicated in paragraph 3.2.2.1.

After incubating for 24 h at 37° C. ±1° C., with shaking (175 rpm), the culture supernatant was collected, and then the PRP concentration was determined by ELISA according to the method described in example 1. The same trial were repeated 3 times. The results are presented in the table below. The values indicated represented the mean value for three trials.

|  | Trial 1 | Trial 2 | Trial 3 |
| --- | --- | --- | --- |
| Stock frozen material Heterogeneous population | 145* | 185 | 116 |
| Daughter frozen material Homogeneous population of capsulated bacteria | 402 | 447 | 429 |

*results expressed in mg/l

Conclusion: the production of PRP by the daughter population consisting of a homogeneous population of capsulated bacteria was improved ≈ by a factor of 3. Consequently, the method which consisted in using a step culture of on a selective solid medium which made it possible to select white colonies containing 100% of capsulated bacteria improved the PRP yields obtained. This method can also be used to constitute a population of completely capsulated bacteria from an initial population which contains a mixture of capsulated and noncapsulated bacteria.

Example 4

Role of the Stabilizing Culture Medium on the Bacterial Population and on the Production of PRP The starting bacterial population consisted of a population of completely capsulated bacteria whose cap locus contained at least two copies of the 18 kb gene and which produced 100% of white colonies on a selective solid medium.

4.1) Operating Protocol

The contents of a frozen material containing per ml from $10^8$ to $10^{10}$ bacteria obtained from the daughter population selected according to the operating protocol of paragraph 3.2.2.1 were inoculated into a 1 liter fermentor containing 500 ml of a liquid medium whose composition is that indicated in paragraph 3.2.2.1. After incubating for 14 hours at 37° C., with shaking, a volume of the first culture was transferred into a second 1 liter fermentor containing 500 ml of the same liquid medium so as to have an initial OD equal to 0.3. After another incubation of ~5 hours under the same conditions (OD value obtained in the region of 4), a volume of the second culture was transferred into a third 1 liter fermentor containing 500 ml of medium so as to have an initial OD equal to 0.3, and then, after incubating for ≈3 hours (OD value obtained in the region of 4), the volume was poured into a fourth 1 liter fermentor containing 500 ml of the same liquid medium. This operating protocol was an adaptation to laboratory scale of the steps which were normally carried out for the industrial production of PRP in a fermentor of 13 000 liters.

The number of bacterial generations was calculated at the end of each culture using the conventional formula N=Log X/X0×1/Log 2 in which X represented the biomass at the end of the culture and X0 the biomass at the start of the culture. The number of cumulative bacterial generations obtained at the end of the fourth culture in a 1 liter fermentor in fact corresponded to the number of bacterial generations obtained at the end of the culture in a 13 000 liter fermentor. At the end of each culture, the cap locus was characterized and the percentage of bacteria which form white colonies on selective solid medium was determined according to the methods described in example 3. The results obtained were grouped together in the table below.

|  | Initial population | Culture 1 | Culture 2 | Culture 3 | Culture 4 |
|---|---|---|---|---|---|
| Number of generations |  | 11.46 | 3.69 | 3.75 | 5.19 |
| cap locus | No non-duplicated form visible during electrophoresis | No non-duplicated form visible during electrophoresis | No non-duplicated form visible during electrophoresis | No non-duplicated form visible during electrophoresis | No non-duplicated form visible during electrophoresis |
| % of white colonies | 100 | 97 | 98 | 99 | 100 |
| PRP (mg/l) |  | 842 | 904 | 719 | 782 |

The number of cumulative generations at the end of the fourth culture is 24.09 generations.

The successive cultures do not modify the characteristics of the bacterial population, which remains completely capsulated during the successive cultures. The production of PRP also remains stable throughout the culture at a very high level. The composition of this medium therefore exercises a stabilizing role on the capsulated bacterial population since the characteristics of the bacterial population do not change appreciably during the culture.

We claim:

1. A *Haemophilus influenzae* serotype b culture medium, wherein the culture medium comprises protoporphyrin IX and at least one plant peptone.

2. The medium as claimed in claim 1 in which the protoporphyrin IX concentration is at least 0.01 mg/l.

3. The medium as claimed in claim 2 in which the protoporphyrin IX concentration is between 0.1 mg/l and 5 mg/l.

4. The medium as claimed in claim 1 in which the plant peptone is a wheat peptone.

5. The medium as claimed in claim 1 in which the plant peptone is a garden pea peptone.

6. The medium as claimed in claim 1 in which the total plant peptone concentration in the culture medium is equivalent to a protein nitrogen concentration of between 0.08 g/l and 2.25 g/l.

7. The medium as claimed in claim 1 wherein the medium is free of contaminants of animal origin.

8. The culture medium as claimed in claim 1, wherein the medium is in liquid form and comprises:

from 0.1 mg/l to 5 mg/l of protoporphyrin IX, and further comprises from 2 to 50 mg/l of β-NAD, from 2 to 20 g/l of glucose, from 2 to 5 g/l of a yeast extract, and $Na^+$, $NH_4^+$, $Ca^{++}$, $Mg^{++}$, $HPO_4^{--}$, $H_2PO_4^-$, $SO_4^{--}$ and $Cl^-$ ions, wherein the plant peptone is a garden pea peptone that is present in amount equivalent to a protein nitrogen concentration of between 0.4 g/l and 1.5 g/l, and wherein the pH of the medium is between 6.5 and 7.5.

9. A solid culture medium for *Haemophilus influenzae* serotype b comprising:

at least 1 mg/l of β-NAD, at least 0.5 mg/l of protoporphyrin IX, a plant peptone and a yeast extract in a sufficient quantity for the protein nitrogen concentration in the medium to be at least 0.2 g/l of protein nitrogen and in a proportion such that the ratio between the quantity of plant peptone and the quantity of yeast extract in the medium is 0.1 to 9 when the protein nitrogen concentration of the medium is 0.2 g/l to 0.8 g/l and is 1 to 9 when the protein nitrogen concentration of the medium is >0.8 g/l, a carbohydrate, a detoxifying agent, and $Na^+$, $K^+$, $Ca^{++}$, $Mg^{++}$, $Fe^{+++}$, $HPO_4^{--}$, $H_2PO4^-$, $SO_4^{--}$ and $Cl^-$ wherein the pH of the medium is between 6.5 and 7.5.

10. A solid medium that comprises:

from 5 to 50 mg/l of β-NAD, from 0.5 to 5 mg/l of protoporphyrin IX, from 1 to 10 g/l of glucose, from 1 to 10 mg/l of Tween 80, from 3 to 4 g/l of $K_2HPO_4$, from 0.9 to 3 g/l of $KH_2PO_4$, from 0.5 to 2 g/l of $K_2SO_4$, from 20 to 500 mg/l of $MgCl_2$, from 2 to 50 mg/l of $CaCl_2.2H_2O$, from 1 to 5 mg/l of $FeCl_3.6H_2O$, from 4 to 8 g/l of NaCl, from 4 to 8 g/l of a yeast extract, and from 4 to 8 g/l of a garden pea peptone such that the ratio between the quantity of garden pea peptone and the quantity of yeast extract is ≥1 when the protein nitrogen concentration of the medium is >0.8 g/l.

11. A method for producing polyribosyl ribitol phosphate (PRP) comprising:

(a) culturing *Haemophilus influenzae* serotype b in the liquid culture medium of any one of claims 1 to 7, (b) collecting culture supernatant from (i), and (c) extracting the PRP from the culture supernatant.

12. A method for producing polyribosyl ribitol phosphate (PRP) comprising:

(i) culturing *Haemophilus influenzae* serotype b on a solid culture medium to produce one or more colonies, (ii) transferring one or more colonies of the one or more colonies produced in (i) from the solid medium to the liquid culture medium of claim 1 and suspending and culturing the colonies in the liquid culture medium, (iii) collecting culture supernatant from the liquid culture medium of (ii), and (iv) extracting the PRP from the culture supernatant.

13. The method as claimed in claim 12, in which the source of protein nitrogen of the solid culture medium is of non-animal origin and comprises at least one plant peptone.

14. The method as claimed in claim 13, in which the plant peptone is a garden pea peptone.

15. The method as claimed in claim 13 in which the solid culture medium comprises a heme consisting of protoporphyrin IX.

16. The method as claimed in claim 15, wherein the solid culture medium and the liquid culture medium are free of contaminants of animal origin.

17. The method as claimed in claim 15, in which the solid medium comprises:
- at least 1 mg/l of β-NAD,
- at least 0.5 mg/l of protoporphyrin IX,
- at least one plant peptone and a yeast extract in a sufficient quantity for the protein nitrogen concentration in the solid medium to be at least 0.2 g/l and in a proportion such that the ratio of the quantity of plant protein to the quantity of yeast extract in the medium is 0.1 to 9 when the concentration of protein nitrogen of the medium is 0.2 g/l to 0.8 g/l and is 1 to 9 when the concentration of protein nitrogen of the medium is >0.8 g/l,
- a carbohydrate,
- a detoxifying agent, and
- $Na^+, K^+, Ca^{++}, Mg^{++}, Fe^{+++}, HPO_4^{--}, H_2PO4^-, SO_4^{--}$ and $Cl^-$ ions, wherein the pH of the medium is between 6.5 and 7.5.

18. The method as claimed in claim 17 in which the solid medium comprises:
- from 5 to 50 mg/l of β-NAD,
- from 0.5 to 5 mg/l of protoporphyrin IX,
- from 1 to 10 g/l of glucose,
- from 1 to 10 mg/l of Tween 80,
- from 3 to 4 g/l of $K_2HPO_4$,
- from 0.9 to 3 g/l of $KH_2PO_4$,
- from 0.5 to 2 g/l of $K_2SO_4$,
- from 20 to 500 mg/l of $MgCl_2$,
- from 2 to 50 mg/l of $CaCl_2.2H_2O$,
- from 1 to 5 mg/l of $FeCl_3.6H_2O$,
- from 4 to 8 g/l of NaCl,
- from 4 to 8 g/l of a yeast extract, and
- from 4 to 8 g/l of a garden pea peptone such that the ratio between the quantity of garden pea peptone and the quantity of yeast extract is ≥1 when the protein nitrogen concentration of the medium is >0.8 g/l.

19. The method as claimed in claim 17 or in claim 18, wherein the colonies that are transferred into the liquid culture medium are white.

20. A method for producing a population of completely encapsulated *Haemophilus influenzae* serotype b bacteria comprising:
(a) Culturing *Haemophilus influenzae* serotype b on a solid medium to produce one or more white colonies, the solid medium comprising:
- from 5 to 50 mg/l of β-NAD,
- from 0.5 to 5 mg/l of protoporphyrin IX,
- from 1 to 10 g/l of glucose,
- from 1 to 10 mg/l of Tween 80,
- from 3 to 4 g/l of $K_2HPO_4$,
- from 0.9 to 3 g/l of $KH_2PO_4$,
- from 0.5 to 2 g/l of $K_2SO_4$,
- from 20 to 500 mg/l of $MgCl_2$,
- from 2 to 50 mg/l of $CaCl_2.2H_2O$,
- from 1 to 5 mg/l of $FeCl_3.6H_2O$,
- from 4 to 8 g/l of NaCl,
- from 4 to 8 g/l of a yeast extract, and
- from 4 to 8 g/l of a garden pea peptone such that the ratio between the quantity of garden pea peptone and the quantity of yeast extract is ≥1 when the protein nitrogen concentration of the medium is >0.8 g/l, and (b) transferring one or more of the white colonies produced in (i) from the solid medium to a liquid culture medium and suspending and culturing the white colonies in the liquid culture medium to produce a bacterial population, the liquid culture medium comprising:
- from 0.1 to 5 mg/l of protoporphyrin IX,
- from 2 to 50 mg/l of β-NAD,
- from 2 to 20 g/l of glucose,
- from 2 to 5 g/l of a yeast extract,
- a garden pea peptone equivalent to a protein nitrogen concentration of 0.4 g/l to 1.5 g/l, and
- $Na^+, NH_4^+, Ca^{++}, Mg^{++}, HPO_4^{--}, H_2PO_4^-, SO_4^{--}$ and $Cl^-$ ions, wherein the pH is between 6.5 and 7.5,
(iii) freezing or freeze-drying the bacterial population produced in (ii).

21. The method as claimed in claim 20, wherein the method is conducted with media free of contaminants of animal origin.

22. A method of producing polyribosyl-ribitol-phosphate (PRP) comprising harvesting PRP produced by the *Haemophilus influenzae* serotype b bacteria population produced according to the method of claim 21.

23. A method for producing polyribosyl ribitol phosphate (PRP) comprising:
(a) culturing *Haemophilus influenzae* serotype b in the liquid culture medium of claim 8,
(b) collecting culture supernatant from (i), and
(c) extracting the PRP from the culture supernatant.

\* \* \* \* \*